(12) United States Patent
Savage

(10) Patent No.: US 9,517,094 B1
(45) Date of Patent: Dec. 13, 2016

(54) INTRAMEDULLARY FIXATION APPARATUS FOR USE IN HIP AND FEMUR FRACTURE SURGERY

(71) Applicant: John Bodeker Savage, Potsdam, NY (US)

(72) Inventor: John Bodeker Savage, Potsdam, NY (US)

(73) Assignee: Savage Medical Design LLC, Potsdam, NY (US)

( * ) Notice: Subject to any disclaimer, the term of this patent is extended or adjusted under 35 U.S.C. 154(b) by 0 days.

(21) Appl. No.: 14/735,068

(22) Filed: Jun. 9, 2015

(51) Int. Cl.
*A61B 17/76* (2006.01)
*A61B 17/72* (2006.01)
*A61B 17/74* (2006.01)

(52) U.S. Cl.
CPC .......... *A61B 17/725* (2013.01); *A61B 17/744* (2013.01)

(58) Field of Classification Search
CPC ...... A61B 17/72; A61B 17/725; A61B 17/744
See application file for complete search history.

(56) References Cited

U.S. PATENT DOCUMENTS

| | | | | |
|---|---|---|---|---|
| 4,212,294 A * | 7/1980 | Murphy | ................. | A61B 17/72 606/64 |
| 4,281,649 A * | 8/1981 | Derweduwen | ..... | A61B 17/1725 606/64 |
| 4,697,585 A * | 10/1987 | Williams | ................. | A61B 17/72 606/64 |
| 4,946,459 A * | 8/1990 | Bradshaw | ........... | A61B 17/7216 606/62 |
| 5,032,125 A * | 7/1991 | Durham | ................. | A61B 17/744 606/309 |
| 5,454,813 A * | 10/1995 | Lawes | ................. | A61B 17/1721 606/62 |
| 6,221,074 B1 * | 4/2001 | Cole | ....................... | A61B 17/72 606/60 |
| 6,402,753 B1 * | 6/2002 | Cole | ....................... | A61B 17/72 606/60 |
| 6,562,042 B2 * | 5/2003 | Nelson | ................ | A61B 17/1721 606/328 |
| 6,648,889 B2 * | 11/2003 | Bramlet | ................ | A61B 17/744 606/310 |
| 7,347,861 B2 * | 3/2008 | Johnstone | ........... | A61B 17/1717 606/62 |

(Continued)

*Primary Examiner* — Mary Hoffman
(74) *Attorney, Agent, or Firm* — Sidney W. Kilgore, P.A.; Sidney W. Kilgore, Attorney

(57) ABSTRACT

An orthopedic intramedullary fixation apparatus and system for use in hip and femur fracture surgery comprises an intramedullary nail, a dynamic lag screw structure comprising a longitudinal sheath and a lag screw, and securing means to fix the intramedullary nail relative to a femur. A dynamic channel created by the lag screw structure allows the lag screw to adjust dynamically, and thereby may permit further compression of the fractured bone to an optimal level as a patient begins to bear weight on it following surgery. Surgical fixation may be expedited, as a favorable point of access for a lag screw may be determined readily, particularly with obese patients in whom access to the trochanter may be problematic. Complications during surgery, such as accidental fracturing of the femoral neck and head and over-penetration of the lag screw may be avoided.

13 Claims, 8 Drawing Sheets

(56) References Cited

U.S. PATENT DOCUMENTS

| | | | | |
|---|---|---|---|---|
| 7,601,153 B2* | 10/2009 | Shinjo | A61B 17/744 | 606/62 |
| 8,206,389 B2* | 6/2012 | Huebner | A61B 17/7225 | 606/62 |
| 9,005,201 B2* | 4/2015 | Munro | A61B 17/7208 | 606/64 |
| 9,320,551 B2* | 4/2016 | Frank | A61B 17/7241 | |
| 2002/0032445 A1* | 3/2002 | Fujiwara | A61B 17/744 | 606/67 |
| 2002/0133234 A1* | 9/2002 | Sotereanos | A61B 17/175 | 623/23.26 |
| 2002/0151898 A1* | 10/2002 | Sohngen | A61B 17/68 | 606/62 |
| 2003/0171819 A1* | 9/2003 | Sotereanos | A61B 17/744 | 623/22.42 |
| 2003/0195515 A1* | 10/2003 | Sohngen | A61B 17/68 | 606/62 |
| 2004/0122428 A1* | 6/2004 | Johnstone | A61B 17/1717 | 606/62 |
| 2005/0069397 A1* | 3/2005 | Shavit | A61B 17/744 | 411/457 |
| 2006/0089642 A1* | 4/2006 | Diaz | A61B 17/70 | 606/60 |
| 2007/0049940 A1* | 3/2007 | Wallace | A61B 17/72 | 606/62 |
| 2007/0100342 A1* | 5/2007 | Green | A61B 17/1717 | 606/64 |
| 2008/0140077 A1* | 6/2008 | Kebaish | A61B 17/744 | 606/64 |
| 2009/0306664 A1* | 12/2009 | Teeny | A61B 17/725 | 606/64 |
| 2009/0326534 A1* | 12/2009 | Yamazaki | A61B 17/7241 | 606/65 |
| 2010/0023011 A1* | 1/2010 | Nakamura | A61B 17/746 | 606/64 |
| 2010/0094292 A1* | 4/2010 | Parrott | A61B 17/7241 | 606/62 |
| 2010/0137863 A1* | 6/2010 | Munro | A61B 17/7208 | 606/64 |
| 2012/0150187 A1* | 6/2012 | Gotfried | A61B 17/1717 | 606/64 |
| 2012/0165871 A1* | 6/2012 | Malone | A61B 17/7064 | 606/247 |
| 2012/0191092 A1* | 7/2012 | Buettler | A61B 17/8891 | 606/64 |
| 2012/0197255 A1* | 8/2012 | Elghazaly | A61B 17/725 | 606/64 |
| 2013/0041414 A1* | 2/2013 | Epperly | A61B 17/7225 | 606/310 |
| 2014/0012259 A1* | 1/2014 | Matityahu | A61B 17/748 | 606/62 |

* cited by examiner

INTRAMEDULLARY FIXATION APPARATUS FOR USE IN HIP AND FEMUR FRACTURE SURGERY

CROSS-REFERENCES TO RELATED APPLICATIONS

This application claims the benefit of U.S. Provisional Application No. 61/990,741, filed 9 May 2014.

STATEMENT REGARDING FEDERALLY SPONSORED RESEARCH OR DEVELOPMENT

Not applicable.

MICROFICHE APPENDIX

Not applicable.

DESCRIPTION

1. Field of Technology

At least some embodiments disclosed herein relate, in general, to the field of orthopaedic implant apparatus and systems for bone and joint surgery, and more specifically, to intramedullary fixation apparatus and systems for certain types of fractures, including, but not limited to, fractures of the hip and femur.

2. Background

An open reduction and internal fixation (ORIF) is a type of orthopaedic surgery used to repair fractured bones. This is a two-part surgery. First, the broken bone is reduced or put back into place. Next, an internal fixation device is placed on or in the bone, or both, typically through the use of screws, plates, rods, pins or nails used to hold the broken bone together. The Dynamic Hip Screw and the Gamma Nail are currently two acceptable fixation apparatus to treat unstable intertrochanteric and sub-trochanteric fractures, which are common in the old osteoporotic patient but can be challenging to fix and problematic to manage.

In the 1980s, perhaps the most common method of fixation employed the Dynamic Hip Screw. Typically, there are three (3) components of a Dynamic Hip Screw, including a dynamic lag screw (inserted into the neck of a femur), a side plate, and a plurality of cortical screws (fixated to proximal or distal femoral shaft, or both). The idea behind this design is that the femoral head component is allowed to move along one plane—a Dynamic Hip Screw allows controlled dynamic sliding of the femoral head component along the construct—and since bone responds to dynamic stresses, the native femur may undergo remodeling and proper fracture healing through compression of the fracture line. A disadvantage of this technique, however, was that the plate was lateral to the load-bearing line of the hip, such that any defect in the medial cortex of the femur, whether due to imperfect reduction, comminution, or a metastasis meant that a varus stress would be applied to the fixation with every weight-bearing step, which could, in turn, cause the cutting-out of the screw from the head of the femur, or failure at the nail-plate junction or of the screws securing the plate to the bone.

An intramedullary appliance, the Zickel Nail, addressed some of these problems, but it proved technically difficult to insert, even in experienced hands, and presented its own problems. Among these was the increased likelihood of fracture at the base of the greater trochanter.

The Gamma Nail is also of an intramedullary fixation design, developed for semi-closed insertion. A Gamma Nail has three principle components: an intramedullary rod (nail) passed down the medullary cavity of the upper shaft of the femur, a lag screw passed through a hole in the proximal part of the rod and from there inserted into the head of the femur, and a set screw which prevents rotation of the main screw. The Gamma Nail itself can be somewhat difficult to place, and biomechanical experiments have suggested that while the sliding ability of the lag screw is maintained in the Gamma Nail, it is decreased in comparison with that of the Dynamic Hip Screw. This may be a particular problem in heavy set or obese patients, for whom it may be difficult to obtain access to the trochanter and find an optimal access point for introduction of a lag screw. Moreover, accidental fracture and over-penetration by the lag screw are not uncommon with the Gamma Nail design, and an optimal level of compression of the fractured bone may not always be obtained during surgery.

BRIEF DESCRIPTION OF THE SEVERAL VIEWS OF THE DRAWINGS

The embodiments illustrated are by way of example, and not limitation, in the figures of the accompanying drawings in which like references indicate similar elements.

DETAILED DESCRIPTION OF THE INVENTION

The following description and drawings are illustrative and are not to be construed as limiting. Numerous specific details are described to provide a thorough understanding. However, in certain instances, well-known or conventional details are not described in order to avoid obscuring the description. References to "one embodiment" or "an embodiment" in the present disclosure are not necessarily references to the same embodiment; and, such references mean at least one.

Reference in this specification to "one embodiment" or "an embodiment" means that a particular feature, structure, or characteristic described in connection with the embodiment is included in at least one embodiment of the disclosure. The appearances of the phrase "in one embodiment" or substantially similar phrases in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

Figure 1:
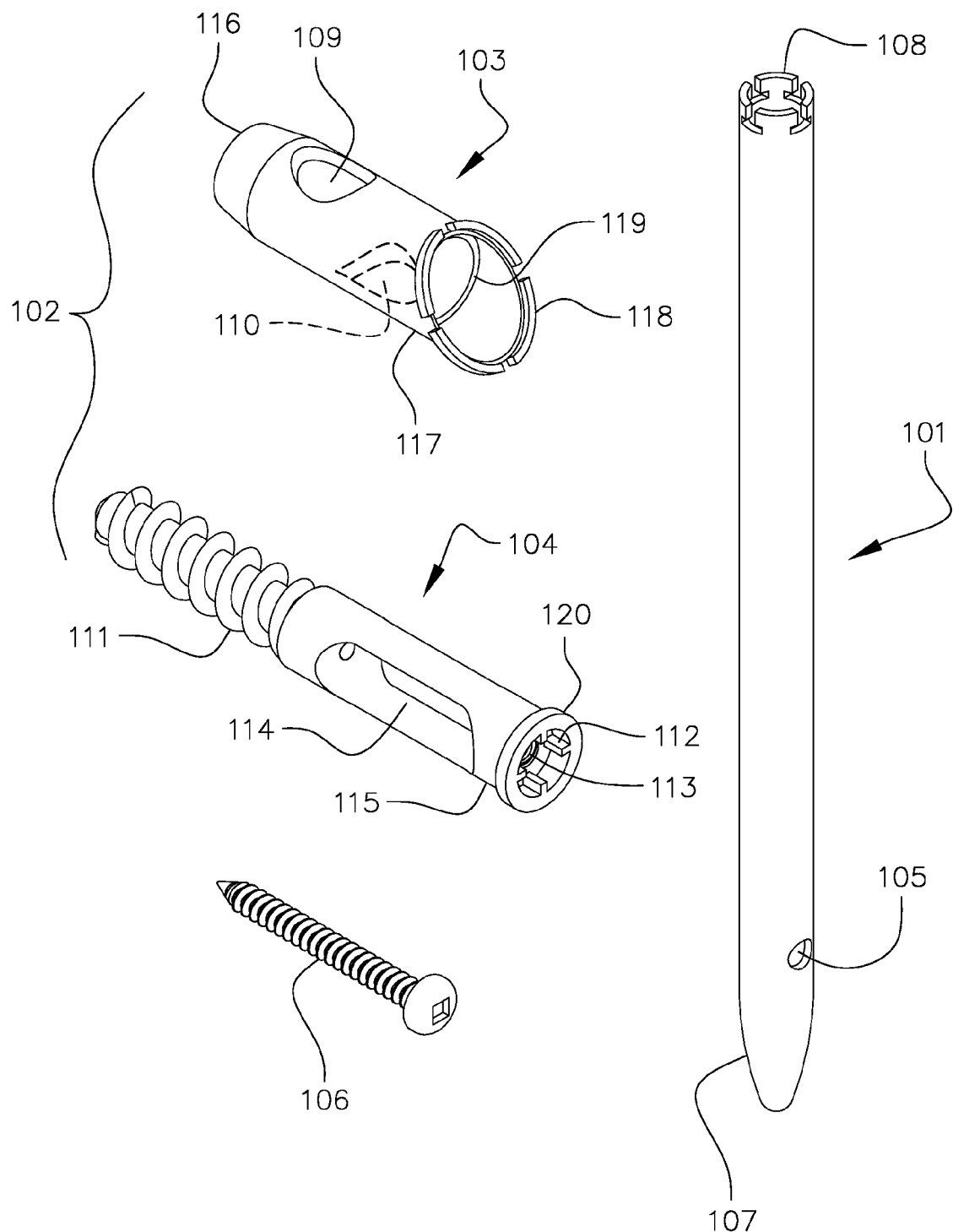
FIG. 1 is an isometric view of an intramedullary nail, a dynamic lag screw structure comprised of a longitudinal sheath and a lag screw, and a surgical screw as a fixation means.

As illustrated in FIG. 1, an embodiment of the system comprises an intramedullary nail (intramedullary rod) 101, a dynamic lag screw structure 102 including a longitudinal sheath 103 open at a distal end 116 and at a proximal end 117 with an upper orifice 109 and lower orifice 110, and further including a lag screw 104 with a longitudinal slot, configured to be inserted into the proximal end of the longitudinal sheath, and may further have some securing means known in the art, such as surgical screws, bolts, or tightrope fixation, configured to keep an intramedullary nail 101 in a proper position relative to a bone. By way of illustration and without limitation, in an embodiment, an intramedullary nail 101 may have one or more lateral orifices 105 passing through it proximally or distally, or both, with respect to a long bone, each such lateral orifice 105 configured to accept one or more surgical screws 106 configured to pass into or through an intramedullary nail 101. As is known in the art, an intramedullary nail 101 may have a solid, semi-solid, or hollow core, may be curved to accommodate the anterior curvature of a femur of a patient, and may be of varying length and proximal and distal diameter, as may be appropriate to a given patient. An intramedullary nail 101 may be tapered at its distal end 107, inter alia, to facilitate insertion, and may be configured at its proximal end 108 to receive a guidance device or comparable instrument known in the art.

In an embodiment, a longitudinal sheath 103 of a dynamic lag screw structure 102 is open at a distal end 116 and at a proximal end 117, with an upper orifice 109 and lower orifice 110, said upper orifice 109 and lower orifice 110 together configured to accept an intramedullary nail 101 and allowing at least a portion of said intramedullary nail 101 to be passed transversely through said longitudinal sheath 103. In an embodiment, the distal end (insertion end) 116 of a longitudinal sheath 103 may be tapered, may have an outer rim at its proximal end 117, and may have an inner lip 119. An outer rim 118 may be configured to ensure that a longitudinal sheath 103 cannot be inserted beyond the lateral cortex of a femur. In an embodiment, a longitudinal sheath 103 may be pressed or tapped into the bone through a hole or channel that has been reamed in a bone.

In an embodiment, a lag screw 104 may employ at its distal end (insertion end) a self-tapping thread 111. In an embodiment, a lag screw 104 may have at its proximal end a drive 112. Said drive 112 may include some form of internal threading 113 or other securing means configured to receive a self-holding screwdriver or comparable tool known in the art. In an embodiment, a lag screw 104 may have longitudinal slot 114 through its shank 115 configured to accept an intramedullary nail 101 and allowing at least a portion of it to pass through said lag screw 104. In an embodiment, a lag screw 104 may have an external lip 120 at its proximal end configured to engage an inner lip 119 of a longitudinal sheath 103 so as to prevent said lag screw 104 from further penetrating the bone.

Figure 2:
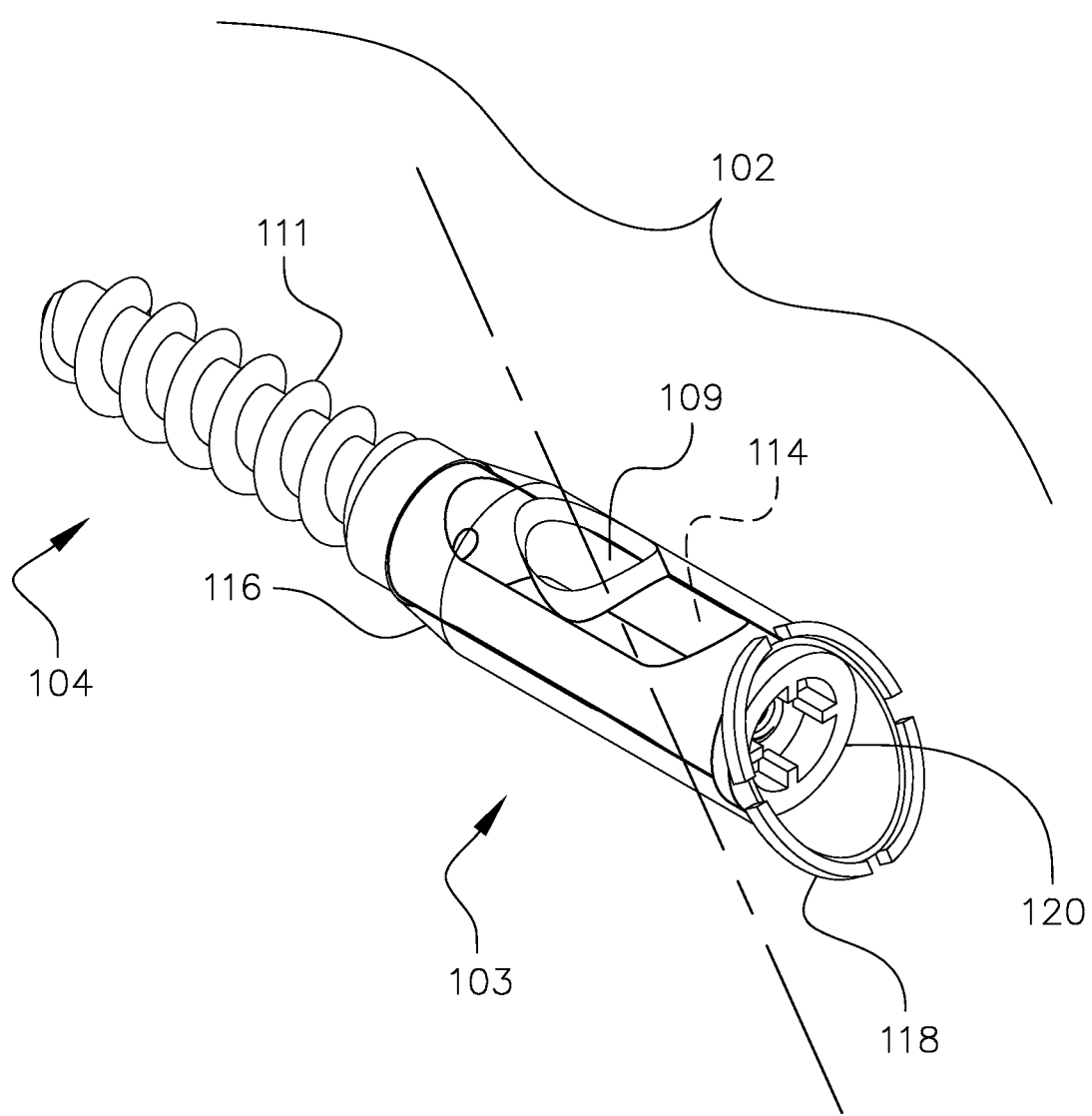
FIG. 2 is cutaway view of a dynamic lag screw structure with a lag screw inserted fully into a longitudinal sheath, revealing a dynamic channel for introduction of an intramedullary nail through the dynamic lag screw structure.

As illustrated in FIG. 2, in an embodiment, a lag screw 104 may be inserted into the proximal end of a longitudinal sheath 103, and at least a portion of an intramedullary nail 101 passed through a dynamic channel formed by the alignment of both an upper orifice 109 and a lower orifice 110 of said longitudinal sheath 103 with a longitudinal slot 114 in the shank 115 of an inserted lag screw 104—said dynamic channel configured to allow movement of said lag screw relative to said intramedullary nail 101 following surgery—and thence into the medullary shaft of a femur. Such a dynamic lag screw structure 102 or comparable structure may be configured to allow the dynamic adjustment of the position of the lag screw 104 in three dimensions—longitudinally, laterally, and normally (i.e., vertically)—relative to the intramedullary nail 101, and hence, to the shaft of the femur and to the neck and head of the femur, respectively, permitting further compression of the fractured bone as a patient begins to bear weight on the joint following surgery.

An embodiment may be comprised of various types of stainless steel, titanium, titanium alloys, biodegradables and other suitable materials, alone or in combination, known in the art.

An embodiment of the current invention allows it to be placed in the hip simply and quickly using an external guidance device or system. Such an initial placement may be thought of as similar to the placement of a screw for in-situ pinning.

Figure 3:
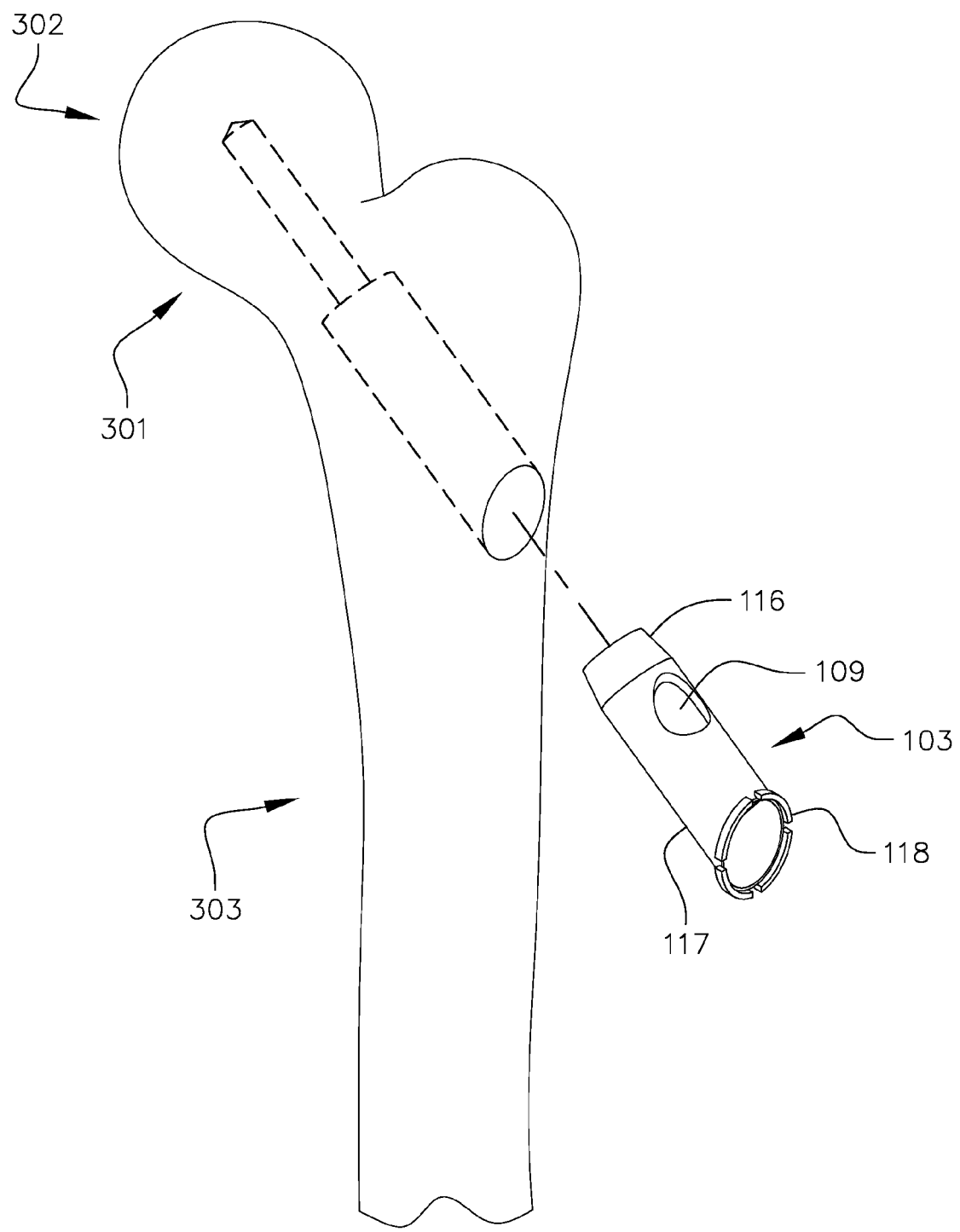
FIG. 3 is an isometric view of a femur, the head and neck of which have been reamed to accept a dynamic lag screw structure, with the longitudinal sheath thereof in position for insertion.
Figure 4:
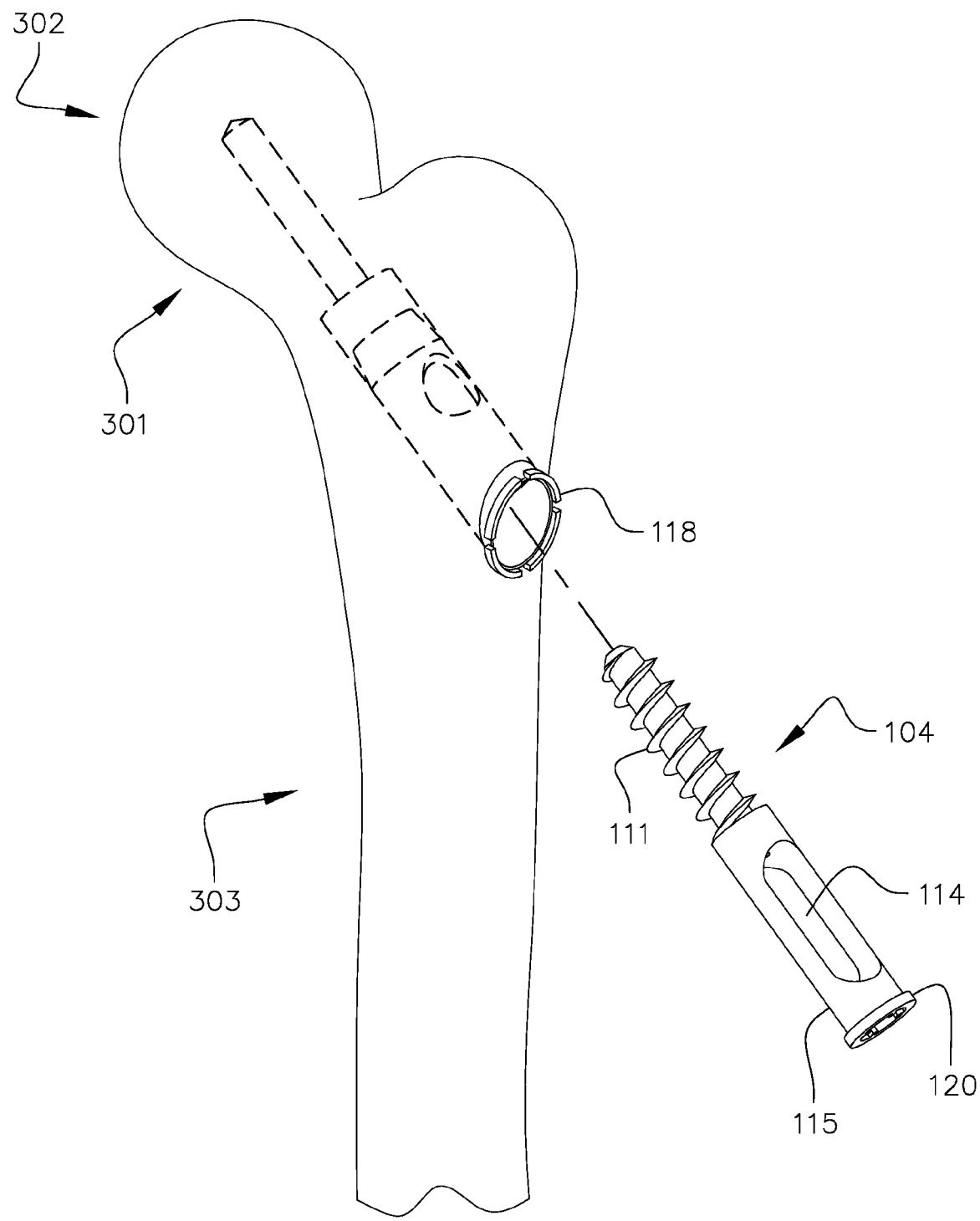
FIG. 4 is an isometric view of a femur into which the longitudinal sheath of a dynamic lag screw structure has been inserted, and the lag screw of the dynamic lag screw structure is in position for insertion within the sheath and thence into the neck and head of the femur.

As illustrated in FIG. 3 and FIG. 4, the neck 301 and head 302 of a femur 303 then may be reamed in a two-step process. First, a channel may be reamed at a desired angle from the lateral cortex of the fractured proximal femur to the center of the head of the fractured proximal femur at the desired depth for the lag screw previously determined. Second, a wider and shorter channel may be reamed at approximately the same angle to accommodate a longitudinal sheath 103. Next, a longitudinal sheath 103 may be pressed or tapped into the bone until any external rim of the sheath reaches the lateral cortex of the fractured proximal femur.

As illustrated in FIG. 3 and FIG. 4, the neck 301 and head 302 of a femur 303 then may be reamed in a two-step process. First, a channel may be reamed at a desired angle from the lateral cortex of the fractured proximal femur to the center of the head of the fractured proximal femur at the desired depth for the lag screw previously determined. Second, a wider and shorter channel may be reamed at approximately the same angle to accommodate a longitudinal sheath 103. Next, a longitudinal sheath 103 may be pressed or tapped into the bone until any external rim of the sheath reaches the lateral cortex of the fractured proximal femur.

Figure 5:
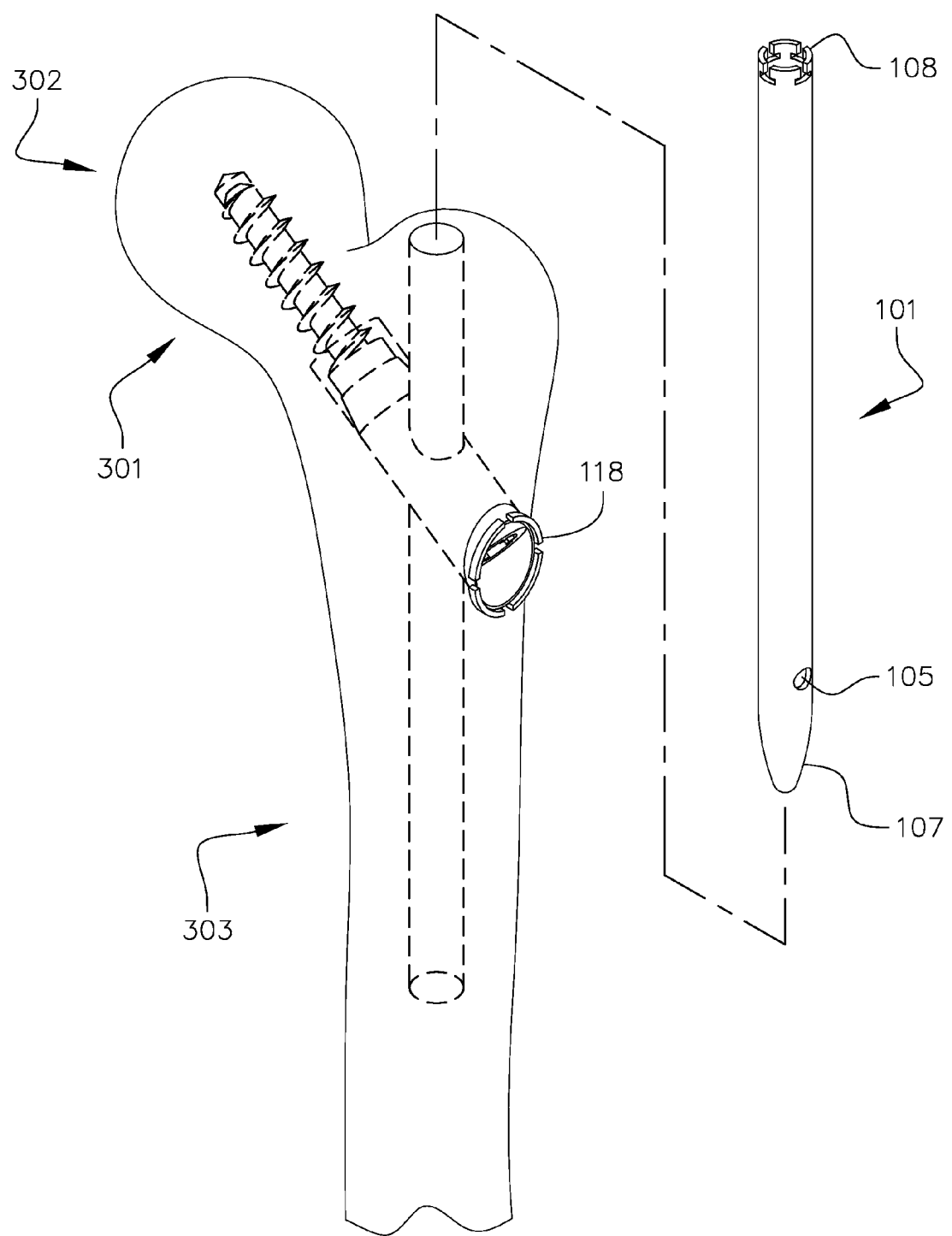
FIG. 5 is an isometric view of a femur, reamed for placement of an intramedullary nail through a dynamic lag screw structure via a dynamic channel created by the alignment of an upper orifice and a lower orifice of a longitudinal sheath with a slot in a lag screw.
Figure 6:
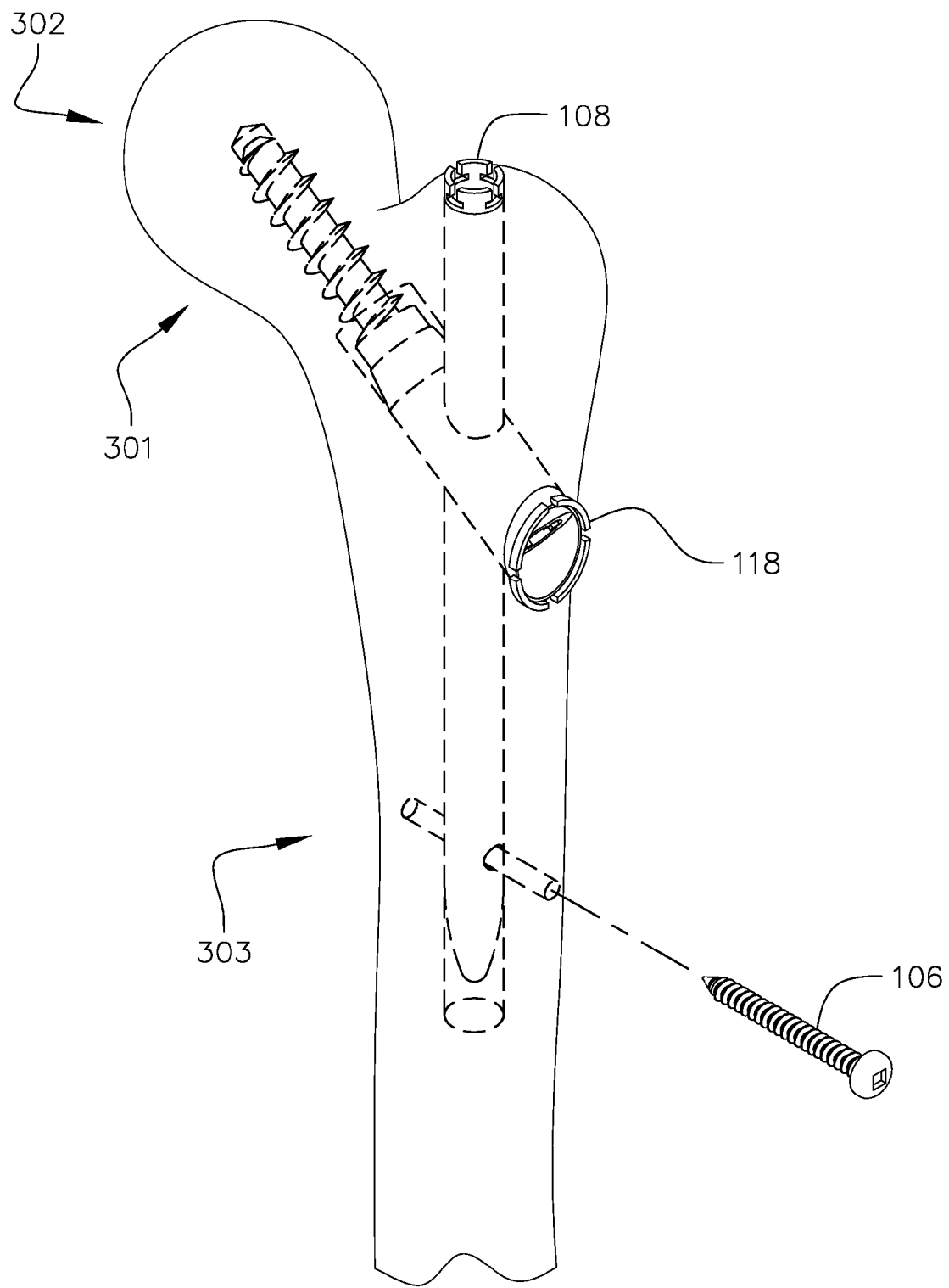
FIG. 6 is an isometric view of a femur into which an intramedullary nail has been inserted through the dynamic lag screw structure, and of a surgical screw in position to be installed distally as a fixation means to secure the intramedullary nail in position with respect to the femur.
Figure 7:
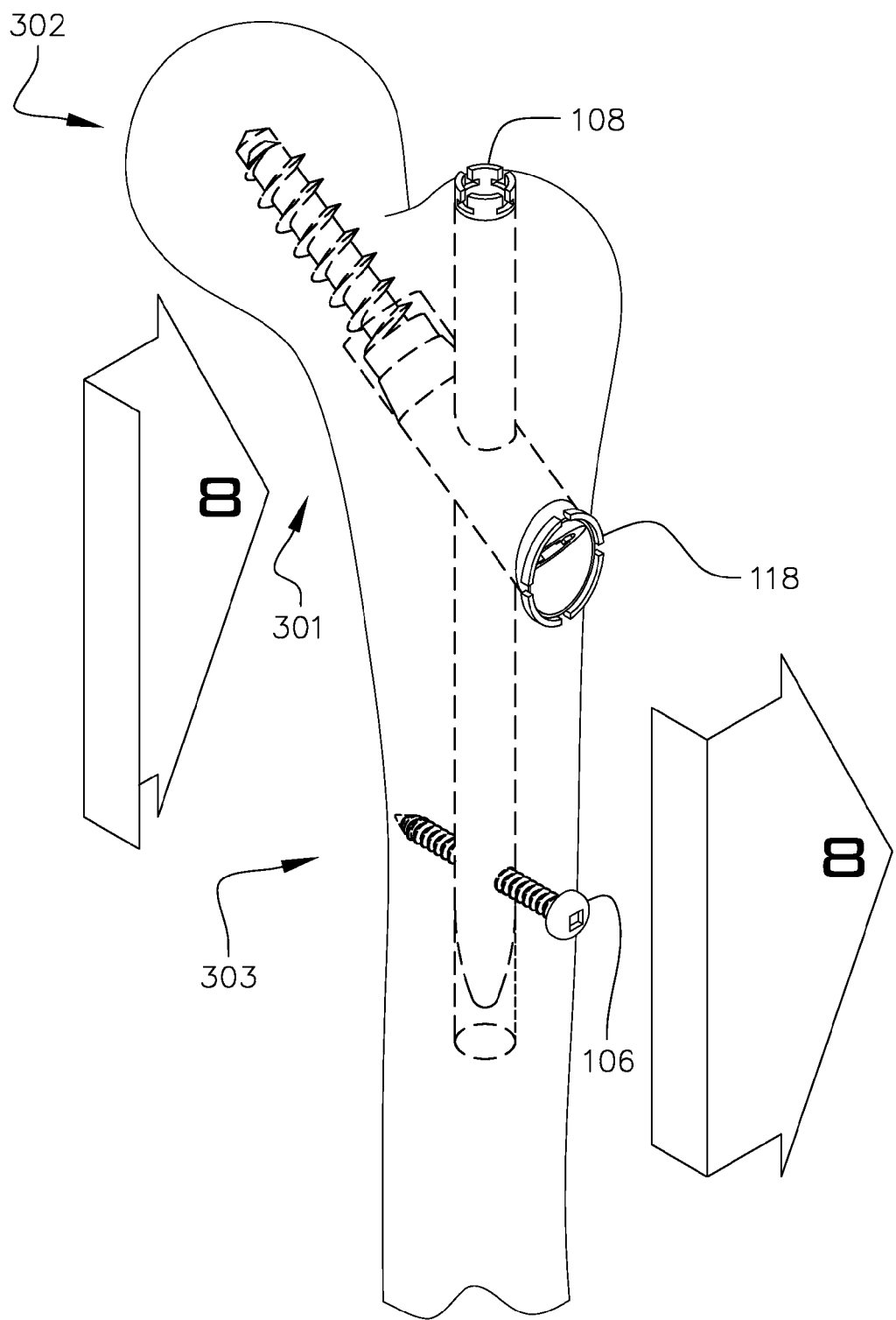
FIG. 7 is an isometric view of a femur into which an intramedullary nail has been inserted through the dynamic lag screw structure, and into which a surgical screw has been inserted distally through a lateral orifice in the intramedullary nail.
Figure 8:
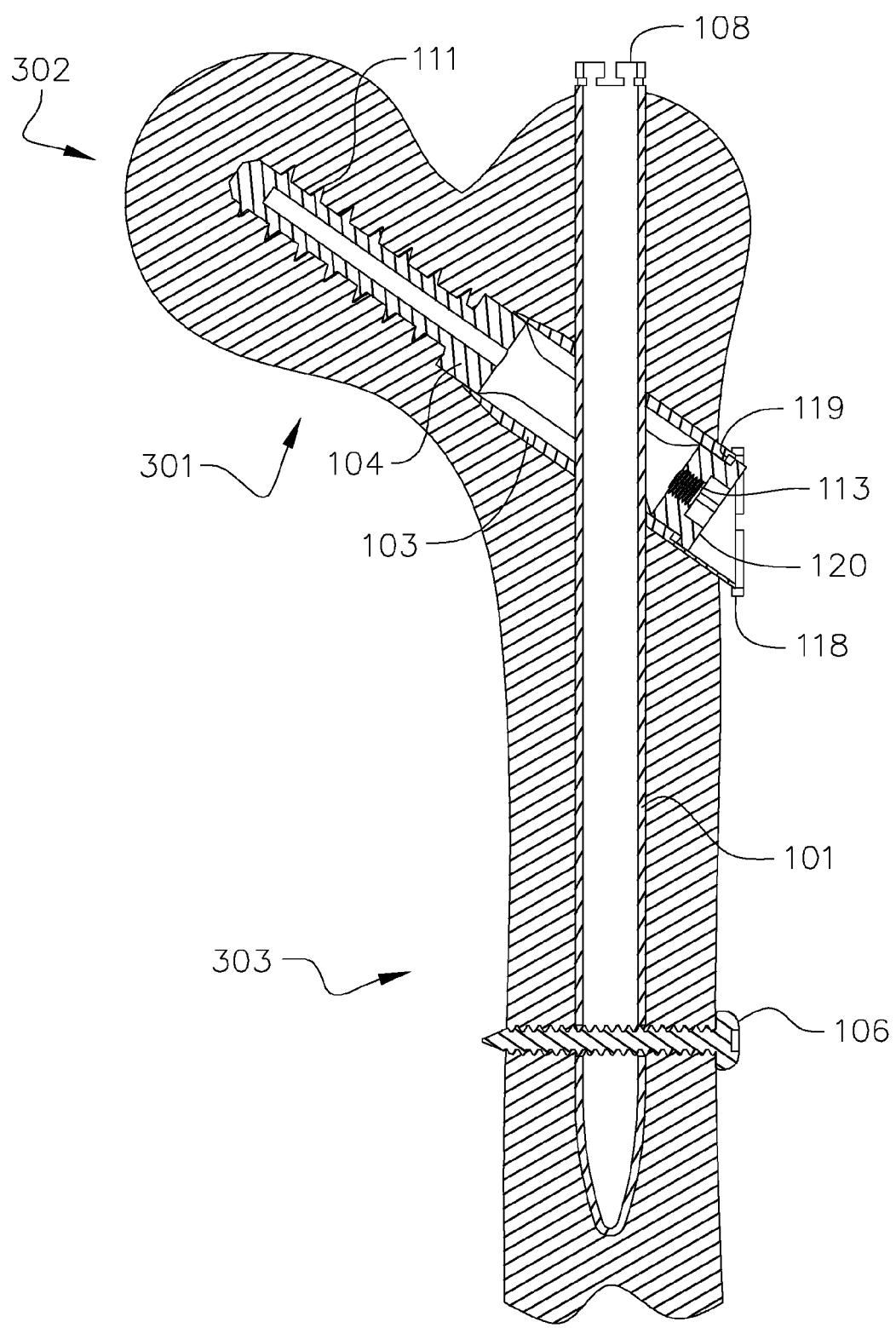
FIG. 8 is a cross-sectional view of an intramedullary nail that has been inserted into the medullary shaft of a femur through the dynamic lag screw structure, revealing an external lip of a lag screw engaged with the inner lip of a longitudinal sheath, and the external rim of a longitudinal sheath engaged against the lateral cortex of the femur.

As illustrated in FIG. 4 and FIG. 5, a lag screw 104, which may have been attached to a self-holding screwdriver or comparable device, may then be inserted into and through the longitudinal sheath 103 embedded in the bone and screwed or otherwise inserted into the neck and head of a femur and into the longer, narrower channel initially reamed. As illustrated in FIG. 6, an upper orifice 109 and a lower orifice 110 in a longitudinal sheath 103 and a slot 114 in a lag screw 104 which has been inserted into a longitudinal sheath 103 may aligned, and the resulting dynamic channel for introduction of an intramedullary nail 101 lined up with the medullary canal of a femoral shaft. A fluoroscope or other guidance device or system then may be used to place an intramedullary nail 101 through the trochanter into the construct and canal of a femur. As depicted in FIG. 6, FIG. 7 and FIG. 8, an intramedullary nail 101 then may be secured to the bone with one or more surgical screws 106 utilizing a fluoroscope or other guidance device or system.

In the foregoing specification, the disclosure has been described with reference to specific exemplary embodiments thereof. The specification and drawings are, accordingly, to be regarded in an illustrative sense rather than a restrictive sense.

I claim:

1. An orthopaedic fixation apparatus comprising:
   a dynamic lag screw structure including a longitudinal sheath open at a distal end and at a proximal end, with an upper orifice and lower orifice, and further including a lag screw with a longitudinal slot, configured to be inserted into the proximal end of the longitudinal sheath such that a dynamic channel is formed by the alignment of said upper orifice and said lower orifice with said longitudinal slot, said dynamic channel configured to accept at least a portion of an intramedullary nail, to be passed transversely through said dynamic channel of said dynamic lag screw structure, and to allow movement of said lag screw relative to said intramedullary nail in three dimensions post implantation of the orthopaedic fixation apparatus;
   an intramedullary nail, at least a portion of which is configured to pass transversely through said dynamic lag screw structure via said dynamic channel; and
   securing means configured to keep said intramedullary nail in a proper position relative to a bone.

2. The orthopaedic fixation apparatus of claim 1, in which said longitudinal sheath is tapered at its distal end.

3. The orthopaedic fixation apparatus of claim 1, in which said longitudinal sheath at its proximal end has an outer rim.

4. The orthopaedic fixation apparatus of claim 1, in which said longitudinal sheath has at its proximal end an inner lip, and said lag screw has an external lip configured to engage said inner lip when said lag screw is inserted into the proximal end of said longitudinal sheath.

5. The orthopaedic fixation apparatus of claim 1, in which the lag screw has a drive with securing means configured to receive a self-holding driver.

6. The orthopaedic fixation apparatus of claim 1, in which said intramedullary nail has at least one lateral orifice passing through it transversely and, at its proximal end, is configured to receive a guidance device.

7. An orthopaedic fixation apparatus comprising:
   a dynamic lag screw structure including a longitudinal sheath open at a distal end and at a proximal end, with an upper orifice and a lower orifice, and further including a lag screw with a longitudinal slot, configured to be inserted into the proximal end of the longitudinal sheath such that a dynamic channel is formed by the alignment of said upper orifice and said lower orifice with said longitudinal slot, said dynamic channel, configured to accept at least a portion of an intramedullary nail, to be passed transversely through said dynamic channel of said dynamic lag screw structure, and said dynamic channel further configured to allow movement of said lag screw relative to said intramedullary nail in three dimensions post-implantation of the orthopaedic fixation apparatus;
   an intramedullary nail, having at least one lateral orifice passing through it, at least a portion of said intramedullary nail configured to pass transversely through said dynamic lag screw structure via said dynamic channel; and
   securing means configured to keep said intramedullary nail in a proper position relative to a bone.

8. The orthopaedic fixation apparatus of claim 7, in which said intramedullary nail is tapered at its distal end.

9. The orthopaedic fixation apparatus of claim 7, in which the longitudinal sheath at its proximal end has an outer rim.

10. The orthopaedic fixation apparatus of claim 7, in which said longitudinal sheath has at its proximal end an inner lip, and said lag screw has an external lip configured to engage said inner lip when said lag screw is inserted into the proximal end of said longitudinal sheath.

11. The orthopaedic fixation apparatus of claim 7, in which the lag screw has a drive with securing means configured to receive a self-holding driver.

12. The orthopaedic fixation apparatus of claim 7, in which the intramedullary nail, at its proximal end, is configured to receive a guidance device.

13. An orthopaedic fixation comprising:
   a dynamic lag screw structure including a longitudinal sheath open at a distal end and at a proximal end, with an upper orifice and a lower orifice, said sheath tapered at its distal end, having an external rim and an inner lip at its proximal end, and further including a lag screw with a longitudinal slot through its shank, a self-tapping thread at its distal end, at its proximal end a drive with internal threading configured to receive a self-holding driver, and an external lip configured to engage said inner lip of said longitudinal sheath, configured to be inserted into the proximal end of the longitudinal sheath such that a dynamic channel is formed by the alignment of said upper orifice and said lower orifice with said longitudinal slot, said dynamic channel configured to accept at least a portion of an intramedullary nail, to be passed transversely through said dynamic-channel of said dynamic lag screw structure, and said dynamic channel further configured to allow movement of said lag screw relative to said intramedullary nail in three dimensions post-implantation of the orthopaedic fixation apparatus;
   an intramedullary nail, having at least one lateral orifice passing through it transversely, configured, at its proximal end to receive a guidance device, and tapered at its distal end, at least of portion of said intramedullary nail configured to pass transversely through said dynamic lag screw structure via said dynamic channel; and
   securing means configured to keep said intramedullary nail in a proper position relative to a bone.

* * * * *